United States Patent [19]
Usui et al.

[11] Patent Number: 5,334,510
[45] Date of Patent: Aug. 2, 1994

[54] PROCESS FOR PRODUCING RIBOFLAVIN BY FERMENTATION

[75] Inventors: Naoki Usui; Yoko Yamamoto; Tuyoshi Nakamatu, all of Kawasaki, Japan

[73] Assignee: Ajinomoto Co., Inc., Tokyo, Japan

[21] Appl. No.: 942,191

[22] Filed: Sep. 9, 1992

[30] Foreign Application Priority Data

Sep. 9, 1991 [JP] Japan .................. 3-227864

[51] Int. Cl.$^5$ .................. C12P 25/00; C12N 1/20
[52] U.S. Cl. .................. 435/66; 435/252.5
[58] Field of Search .................. 435/66

[56] References Cited

U.S. PATENT DOCUMENTS 3,900,368  9/1975  Enei et al. .................. 435/66
4,165,250  8/1979  Epstein et al.

FOREIGN PATENT DOCUMENTS 890917   4/1982   Denmark.
2204687  5/1974   France.
2546907  12/1984  France.

OTHER PUBLICATIONS

Matusi et al *Agric Biol Chem* 46(8) p. 2003-2008 1982 Riboflavin Production By Roseoflavin-resistant . . . .

*Primary Examiner*—Herbert J. Lilling
*Attorney, Agent, or Firm*—Oblon, Spivak, McClelland, Maier & Neustadt

[57] ABSTRACT

The present invention provides a process for producing riboflavin by fermentation, a method for providing microorganisms having an improved riboflavin-producing capability, and strains of microorganisms having improved riboflavin-producing ability. The strains of the present invention belong to the genus Bacillus, have reduced activity of hydrolysing phosphoric acid from 5'-guanylic acid, and have the ability of producing riboflavin. Mutants used in the processes of this invention have an improved ability of producing riboflavin and are capable of producing or accumulating a large amount of riboflavin in the culture medium. The processes of this invention are therefore suitable for producing riboflavin in an effective manner at a low cost.

2 Claims, No Drawings

PROCESS FOR PRODUCING RIBOFLAVIN BY FERMENTATION

BACKGROUND OF THE INVENTION

1. Field of the Invention

The present invention relates to a process for producing riboflavin by fermentation, to a method for providing microorganisms having an improved riboflavin-producing capability, and to strains of microorganisms having improved riboflavin-producing ability. Riboflavin is a isoalloxazine derivative which is used as a vitamin, a medicament for beriberi, a feed additive for livestock and poultry, and a colorant for food.

2. Discussion of the Background

Riboflavin has previously been produced by fermentation processes in which *Eremotheium ashbyii, Ashbya gossypii, Candida flalerii* or *Bacillus subtilis* is cultured in a carbohydrate-containing medium and riboflavin accumulates in the culture medium (*Progress in Industrial Microbiology*, Vol. 1, p. 139 (1959); Belgian Patent No. 890,917; and Japanese Patent Publication No. 10,155/78). These microorganisms, however, produce riboflavin only in low concentration or produce it only very slowly. They are, therefore, not satisfactory in a method for commercially producing riboflavin.

SUMMARY OF THE INVENTION

It is an object of the present invention to provide a process for producing riboflavin through an efficient and inexpensive fermentation.

It is another object of the present invention to provide a method for producing microorganisms having an improved riboflavin-producing capability.

It is another object of the present invention to provide microorganisms having an improved riboflavin-producing capability.

In order to achieve these objects, the inventors undertook an intensive program of research and found that the above objectives can be met by mutant strains which belong to the genus Bacillus, which have reduced activity of hydrolysing phosphoric acid from 5'-guanylic acid (hereinafter referred to as "5'-GMP"), and which have the ability to produce riboflavin. These strains produce riboflavin quickly and in high concentration. Such results have not been obtained in the prior art.

Accordingly, the present invention provides a process for producing riboflavin by fermentation which comprises culturing, in a liquid medium, a mutant strain which belongs to the genus Bacillus, which has both reduced activity of hydrolysing phosphoric acid from 5'-GMP and the ability to produce riboflavin.

Additionally, the present invention provides a process for producing microorganisms having an improved riboflavin-producing capability which comprises mutating a parent strain of Bacillus with a mutagen and selecting for those mutant strains, which have both reduced activity of hydrolysing phosphoric acid from 5'-GMP and the ability to produce riboflavin.

The present invention also provides microorganisms which produce elevated concentrations of riboflavin by fermentation.

DETAILED DESCRIPTION OF THE PREFERRED EMBODIMENTS

One embodiment of the present invention is a process for producing riboflavin by fermentation by culturing a microorganism which belongs to the genus Bacillus, which has reduced activity of hydrolysing phosphoric acid from 5'-GMP and which is capable of producing riboflavin. Mutant strains having a further improved riboflavin-producing capability can be obtained by providing such a microorganism with other properties (e.g., resistance to nucleic acid base analogs) known to be effective for the enhancement of riboflavin-producing ability (see Japanese Patent Publication No. 10,155/78).

As an example of a mutant strain of the present invention, the microorganism *Bacillus subtilis* AJ12644 (FERM BP-3855) may be cited. This strain requires adenins, is deficient in GMP reductase, is resistant to (putins+ azaxanthine) and has reduced activity of hydrolysing phosphoric acid from 5'-GMP.

Another embodiment of the present invention is a method for producing a microorganism having an improved riboflavin-producing capability. In this method, parent strains of microorganisms of the genus Bacillus are mutated to produce mutant strains, which are selected for reduced activity of hydrolysing phosphoric acid from 5'-GMP and the ability to produce riboflavin.

Strains belonging to the genus Bacillus can be used as a parent for obtaining such a mutant. As a specific example of a suitable parent, the riboflavin-producing bacterium *Bacillus subtilis* AJ12643 (FERM BP-3856) may be cited. This strain requires adenins, is deficient in GMP reductase and is resistant to (purine+azaxanthine).

Mutant strains of the present invention can be obtained by applying to a suitable parent strain a conventional mutation inducing technique, for example, irradiation with X-rays or ultraviolet rays, or contact with a mutagenic agent, such as, N-methyl-N'-nitrosoguanidine or other mutagen.

For purposes of the present invention, mutant strains having reduced activity of hydrolysing phosphoric acid from 5'-GMP refers to strains of microorganisms in which the amount of hydrolysis of phosphoric acid from 5'-GMP calculated by $\mu$dmol/min/mg-protein is less than the corresponding value for the parent strain from which the mutant is derived. The amount of hydrolysis of phosphoric acid from 5'-GMP is determined by quantitatively analyzing guanosine via high performance liquid chromatography (HPLC). HPLC is carried out on a CPK-08 column (Mitsubishi Kasei Corp.) with an eluent of 3% lithium formate at pH 4.75 and detected by UV absorption at 260 nm.

In a preferred embodiment, the amount of hydrolysis of phosphoric acid from 5'-GMP is 0.100 $\mu$mol/min/mg-protein or less. In a more preferred embodiment, the amount of hydrolysis of phosphoric acid from 5'-GMP is 0.050 $\mu$mol/min/mg-protein or less. In a still more preferred embodiment, the amount of hydrolysis of phosphoric acid from 5'-GMP is 0.030 $\mu$mol/min/mg-protein or less.

In the production of riboflavin using the mutant strains of the present invention, there can be used an ordinary liquid medium containing carbon sources, nitrogen sources, inorganic salts and, where necessary, minor organic nutrients, as well as nutrients required by the microorganisms. Any carbon source is suitable, provided that it is assimilable by the mutant strains. Examples of usable carbon sources include glucose, sucrose, molasses, hydrolyzed products of starch, and the like. Examples of usable nitrogen sources include ammonium sulfate, urea, ammonia and the like. Examples of minor organic nutrients include amino acids, vitamins, fatty acids and nucleic acids. It is also possible to use other materials that contain minor organic nutrients, for example, yeast extract, peptone, casamino acid, and hydrolyzed products of soybean proteins.

Culturing can be carried out with aeration at a temperature of 30° to 40° C., preferably at 34° to 37° C. The pH of the culture medium is maintained at 6.0 to 7.5, preferably 6.5 to 7.0, both at the beginning and during the course of the culturing. For the adjustment of the pH, there can be used an organic or inorganic acid, or an alkaline substance, including urea, calcium carbonate, ammonia gas, zinc and the like. Thus, a marked quantity of riboflavin can be produced and accumulated in the medium in 1 to 5 days.

After the cultivation, riboflavin can be recovered from the medium in accordance with known procedures. For example, after the removal of the cell bodies by an appropriate procedure (for example, centrifugation), an appropriate quantity of hydrosulfite is added. The appropriate quantity of hydrosulfite is that amount of hydrosulfite which reduces riboflavin to its reduced form. The resulting mixture is slightly stirred and then subjected to centrifugation at 20° C. to collect crude crystals of reduced riboflavin. The crude crystals are suspended in 1N acetic acid solution and dissolved by heating. Impurities are then removed by filtration, and the filtrate cooled to allow crystals to precipitate. The crystals are then collected by filtration and dried to give crystals of desired riboflavin.

Riboflavin is synthesized in vivo from a nucleotide intermediate, such as, 5'-inosine monophosphate (5'-IMP), 5'guanosine monophosphate (5'-GMP) and 5'-guanosine triphosphate (5'-GTP). The present inventors hypothesize that, if a microorganism has a high activity of hydrolysing phosphoric acid from 5'-nucleotides, 5'-nucleotides are dephosphorylated and released from the cell. Presumably, the mutant strains of the present invention, which have reduced activity of hydrolysing phosphoric acid from 5'-nucleotides, are provided with larger quantities of precursors for synthesizing riboflavin and, as a result, riboflavin accumulates in increased quantities.

Other features of the invention will become apparent in the course of the following descriptions of exemplary embodiments which are given for illustration of the invention and are not intended to be limiting thereof.

EXAMPLES

Example 1

Into a liquid nutrient medium (pH 7.0) containing 2.5% of soluble starch, 0.3% of yeast extract, 0.3% of polypeptone and 0.1% of sodium chloride was inoculated riboflavin-producing Bacillus subtilis AJ12643 (FERM BP-3856), which is an adenine-requiring microorganism derived from Bacillus subtilis ATCC 13952, deficient in GMP reductase and resistant to (purine+8-azaxanthine). The microorganism was shake cultured at 34° C. for 16 hours, and 1 ml of the resulting culture was inoculated into 4 ml of nutrient medium having the same composition as above and further shake cultured at 34° C. When the turbidity of the culture at 562 nm increased to 0.8, the cells were collected by centrifugation and washed with 50 mM of phosphate buffer (pH 7.0). The washed cell bodies were suspended in 5 ml of 50 mM phosphate buffer (pH 7.0) containing 500 μg of N-methyl-N'-nitro-N-nitrosoguanidine. The resulting suspension was allowed to stand with ice-cooling for 40 minutes. The thus treated cells were washed with 50 μM of phosphate buffer (pH 7.0), redispersed into 5 ml of 50 mM of phosphate buffer (pH 7.0) and then smeared on an agar plate medium containing the same nutrient composition as above. After culturing at 34° C. for 2 days, the growth of colonies was confirmed. Thereafter, a filter paper dipped with disodium 4-nitrophenyl phosphate solution/50 mM tris buffer (pH 8.8) was placed on the plate, and the plate and the filter paper were allowed to stand at room temperature for 5 minutes. Since colonies of strains having a high activity of hydrolysing phosphoric acid from 5'-GMP are colored yellow, strains having a reduced activity of hydrolysing phosphoric acid from 5'-GMP were selected as those colonies developing only a weak yellow color.

The parent strain (Bacillus subtilis AJ12643) and the mutants obtained by the above procedure were separately inoculated on liquid nutrient media having the above-described composition and shake cultured at 34° C. for 16 hours. The cells were then collected by centrifugation and washed with physiological salt solution. The cells were then suspended and treated by a ultrasonic homogenizer at an output of 200 W for 7 minutes. The resulting solution containing the homogenized cells was added to a solution of 40 mM (final concentration) of 5'-GMP in 200 mM MOPS buffer (pH 7.0), and the reaction was allowed to proceed at 34° C. for 2 hours. The activity of the strains for hydrolysing phosphoric acid from 5'-GMP was determined by quantitatively analyzing guanosine by means of high performance liquid chromatography (CPK-08 column produced by Mitsubishi Kasei Corp.; eluent, 3% lithium formate (pH 4.75); detection, UV at a wavelength of 260 nm).

In a second experiment, the strains were inoculated into the above-described liquid nutrient medium (4 ml) and cultivated at 34° C. for 16 hours. The resulting cultures were inoculated into a medium having the composition set forth in Table 1 (quantity of inoculation=5% by weight) and cultivated at 34° C. for 3 days, and the riboflavin-producing capability of the strains was determined.

TABLE 1

| Components | Concentration |
| --- | --- |
| Glucose | 80 g/l |
| NH$_4$Cl | 15 g/l |
| KH$_2$PO$_4$ | 0.2 g/l |
| MgSO$_4$.7H$_2$O | 0.4 g/l |
| Fe$^{2+}$ | 2 mg/l |
| Mn$^{2+}$ | 2 mg/l |
| RNA | 1.2 g/l |
| CaCl$_2$.2H$_2$O | 2 g/l |
| Mi-eki mixture* | 40 ml/l |
| (Soybean protein hydrolyzate) | |
| L-glutamic acid | 10 g/l |
| L-methionine | 0.3 g/l |
| pH | 7.5 |

*Product of Ajinomoto Corp.

The results obtained for both sets of experiments are shown in Table 2. As is seen from this table, those mutant strains obtained, which had a reduced activity of hydrolysing phosphoric acid from 5'-GMP, were capable of accumulating riboflavin in greater quantities, relative to the parent strain, Bacillus subtilis AJ12643.

TABLE 2

| Strain | Amount of Hydrolysis of Phosphoric Acid From 5'-GMP ($\mu$mol/min/mg-protein) | Amount of Riboflavin Accumulated (g/l) |
| --- | --- | --- |
| AJ12643 | 0.127 | 0.12 |
| No. 25 | 0.063 | 0.24 |
| No. 141 | 0.081 | 0.21 |
| No. 189 | 0.075 | 0.28 |
| No. 235 | 0.077 | 0.24 |

One of the mutant strains obtained above (*Bacillus subtilis* No. 189) was further subjected to mutation-inducing treatment as above, to obtain *Bacillus subtilis* AJ12644 (FERM BP-3855), which had further reduced activity of hydrolysing phosphoric acid from 5'-GMP. In Table 3 are shown the activity for hydrolysing phosphoric acid from 5'-GMP and the quantity of riboflavin accumulated in culture broth for both the parent strain (No. 189) and the resultant mutant strain (AT12644).

TABLE 3

| Strain | Amount of Hydrolysis of Phosphoric Acid From 5'-GMP ($\mu$mol/min/mg-protein) | Amount of Riboflavin Accumulated (g/l) |
| --- | --- | --- |
| No. 189 | 0.075 | 0.24 |
| AJ12644 | 0.020 | 0.90 |

Example 2

In a 5 liter fermentation tank were placed 2 liters of a medium having a composition set forth in Table 4, and the medium was heated and sterilized at 121° C. for 15 minutes. Into this medium were inoculated 100 ml of culture prepared by cultivating *Bacillus subtilis* AJ12644 in a liquid medium at 34° C. for 16 hours, and culturing was carried out at a temperature of 34° C. for 3 days with aeration of 0.5 vvm and stirring at 700 rpm, during which the pH of the medium was maintained at 6.5 by use of ammonia. From this, there was obtained 1.8 liters of culture medium containing 1.05 g/l of riboflavin. The cell bodies were removed from the culture by centrifugation, and then 20 g of hydrosulfite was added. After being slightly stirred, the mixture was subjected to centrifugation to obtain 1.8 g of crude crystals of reduced riboflavin. The crude crystals were suspended in 500 ml of 1N acetic acid solution and oxidized by adding a small quantity of saturated permanganate solution. The resulting mixture was then boiled to dissolve precipitated crystals and then hot-filtered. After cooling, precipitated crystals were collected by filtration to give 750 mg of riboflavin. The product was then recrystallized to obtain 560 mg of pure crystals of riboflavin.

TABLE 4

| Components | Concentration |
| --- | --- |
| Glucose | 80 g/l |
| NH$_4$Cl | 15 g/l |
| KH$_2$PO$_4$ | 0.2 g/l |
| MgSO$_4$.7H$_2$O | 0.4 g/l |
| Fe$^{2+}$ | 2 mg/l |
| Mn$^{2+}$ | 2 mg/l |
| RNA | 1.2 g/l |
| CaCl$_2$.2H$_2$O | 2 g/l |
| Mi-eki mixture* (Soybean protein hydrolyzate) | 40 ml/l |
| L-glutamic acid | 10 g/l |
| L-methionine | 0.3 g/l |
| pH | 7.5 |

*Product of Ajinomoto Corp.

The mutant strains of the present invention have an improved ability to produce riboflavin and are capable of producing and accumulating a markedly larger amount of riboflavin, relative to the prior art. The processes of the present invention producing and employing such mutant strains are therefore suitable for producing riboflavin in an effective manner at a lower cost.

Obviously, numerous modifications and variations of the present invention are possible in light of the above teachings. It is therefore to be understood that within the scope of the appended claims, the invention may be practiced otherwise than as specifically described herein.

What is claimed as new ad desired to be secured by letters patent of the United States is:

1. A process for producing riboflavin by fermentation which comprises:

culturing a biologically pure mutant of *Bacillus subtilis* having an activity of hydrolysing phosphoric acid from 5'-guanylic acid at a rate of 0.1 $\mu$mol/min/mg-protein or less and which has the ability to produce riboflavin; accumulating riboflavin in the medium and recovering the riboflavin.

2. The process of claim 1, in which the mutant is *Bacillus subtilis* AJ 12644.

* * * * *

UNITED STATES PATENT AND TRADEMARK OFFICE
CERTIFICATE OF CORRECTION

PATENT NO. : 5,334,510
DATED : August 2, 1994
INVENTOR(S) : Naoki USUI et al.

It is certified that error appears in the above-identified patent and that said Letters Patent is hereby corrected as shown below:

COLUMN 2, line 14 "adenins" should read --adenine--;
line 15 "putins" should read --purine--;
line 28 "adenins" should read --adenine--;
line 42 "$\mu$dmol" should read --$\mu$[d]mol--.

Signed and Sealed this

Twenty-third Day of May, 1995

Attest:

BRUCE LEHMAN

Attesting Officer    Commissioner of Patents and Trademarks